United States Patent [19]

McWilliams

[11] 4,312,447
[45] Jan. 26, 1982

[54] METHOD AND APPARATUS FOR ENUMERATIVE DISPLAY AND DISPOSAL OF SURGICAL SPONGES

[76] Inventor: Rose M. McWilliams, 1065 S. Josephine, Denver, Colo. 80209

[21] Appl. No.: 127,121

[22] Filed: Mar. 4, 1980

Related U.S. Application Data

[63] Continuation-in-part of Ser. No. 17,903, Mar. 5, 1979.

[51] Int. Cl.³ .................. A61B 19/00; A61F 13/00
[52] U.S. Cl. .................. 206/370; 206/438; 220/90
[58] Field of Search .......... 206/370, 362, 438, 63.5; 220/90

[56] References Cited

U.S. PATENT DOCUMENTS

| | | | |
|---|---|---|---|
| 2,873,052 | 2/1959 | Atherton | 220/90 |
| 3,337,042 | 8/1967 | Bergendal et al. | 206/63.5 |
| 3,481,462 | 12/1969 | Chapel | 206/438 |
| 3,613,899 | 10/1971 | Schleicher | 206/438 |
| 3,727,792 | 4/1973 | Levin | 220/90 |
| 3,765,564 | 10/1973 | Persson | 220/90 |
| 3,948,390 | 4/1976 | Ferreri | 206/370 |
| 4,020,968 | 5/1977 | Chiavola et al. | 220/90 |
| 4,190,153 | 2/1980 | Olsen | 206/63.5 |

*Primary Examiner*—William T. Dixson, Jr.
*Attorney, Agent, or Firm*—Ancel W. Lewis, Jr.

[57] ABSTRACT

Apparatus for enumerative display and disposal of surgical sponges comprising a circular one piece molded plastic article adapted to be fit over the rim of a standard surgical kick bucket and a bag placed in the kick bucket. The article bears a predetermined number of notches in its upper portion for display of sponges draped over the notches, so that when each notch bears a sponge, the number of used sponges on the article is known. The article contains a number of other features including a circumferential fluid receiving portion, shoulder portions, and a tapered annular channel portion to receive a bucket handle, and tapered projections in the notch portions to improve retaining engagement of the sponges. The article is designed to be nestable for easy packaging, sterilizable, inexpensive, and disposable.

9 Claims, 5 Drawing Figures

METHOD AND APPARATUS FOR ENUMERATIVE DISPLAY AND DISPOSAL OF SURGICAL SPONGES

CROSS REFERENCE TO RELATED APPLICATION

This is a continuation-in-part of U.S. Ser. No. 017,903, filed Mar. 5, 1979.

BACKGROUND OF THE INVENTION

The present invention relates to surgical equipment and more particularly to equipment for the disposal of surgical sponges in the operating room.

During a surgical procedure, numerous pliable and disposable articles, termed generally herein sponges, are used to absorb blood or other fluids encountered during the procedure. Personnel using the sponges toss used sponges generally in the direction of one or more buckets placed about the operating room to receive and store the used sponges. These buckets are termed kick buckets in that they are mounted on wheels to be moved by the foot about the operating room. It remains for an operating room nurse or technician to gather up and place in the bucket the used sponges, which, at the end of the procedure, must be tediously withdrawn from the bucket and counted to ensure that all sponges used during the procedure have been accounted for. After the sponges have been removed from the bucket and counted, they may be weighed to determine the amount of blood lost during the procedure. They are then placed in plastic bags for disposal. Besides being tedious, the presently used procedures expose the aseptic environment of the operating room to sponges which may be contaminated.

It is therefore an object of the present invention to provide a method and apparatus by which sponges may be efficiently counted and disposed of.

It is another object of the present invention to provide a method and apparatus by which sponges may be counted and disposed of in a manner which improves the overall environment of the operating room.

SUMMARY OF THE INVENTION

In accordance with the broader aspects of the present invention, a molded plastic article is adapted to display sponges draped over the article in a predetermined number of notches so that, when all notches are filled, the number of sponges on the bucket is known. The preferred apparatus for enumerative display and disposal of surgical sponges comprises a bucket, such as a standard operating room kick bucket, to which is fitted a one piece molded plastic article having an upwardly extending annular central portion with opposed inner and outer sidewalls extending downwardly from a notched upper surface to define a channel in which the rim of the bucket is received to substantially the depth of the notched upper surface. The notched upper surface defines a predetermined number of circumferentially spaced notch portions each comprising a pair of acutely angled side surfaces. The number and size of the notch portions are chosen to enumeratively display sponges draped over the notches. The article further comprises an annular fluid receiving portion extending circumferentially upwardly and outwardly from an outer sidewall portion to define an annular, fluid receiving portion for receiving blood or other fluids from sponges draped over the notches. In order to be sturdily supportively fitted over the bucket, the article preferably further comprises shoulder portions and a channel of greater width in one portion than in another to receive a handle portion of the bucket. The notch portions are divided into two different sizes for different sized sponges. According to the presently used sponge axis, arrays of five large notches and ten smaller notches each extending circumferentially about one half of the articles are preferred. To improve retaining engagement between the sponges and the notches, tapered projections may be provided in the base surfaces of the notches, particularly in the smaller notches.

In use, the bucket is fitted with a disposable plastic bag or lining which provides lining means for receiving fluids from the sponges. The lining is pulled over the rim of the bucket, and the article is fitted over the bag and the bucket. The present method comprises: placing a disposable lining in the bucket; fitting the article over the disposable lining and the bucket; placing one sponge in each notch until each notch is filled; and then removing the sponges from the notches and placing them in a smaller bag. After the surgical procedure, the number of smaller bags is counted, and the bags are placed in the lining means for disposal.

In another embodiment according to the present invention, a disposable plastic bag or lining is itself formed into the above described notched annular central portion and annular fluid receiving portion. In this embodiment, the plastic bag is provided with a rigid or semi-rigid structure.

DESCRIPTION OF THE PREFERRED EMBODIMENT

Figure 1:
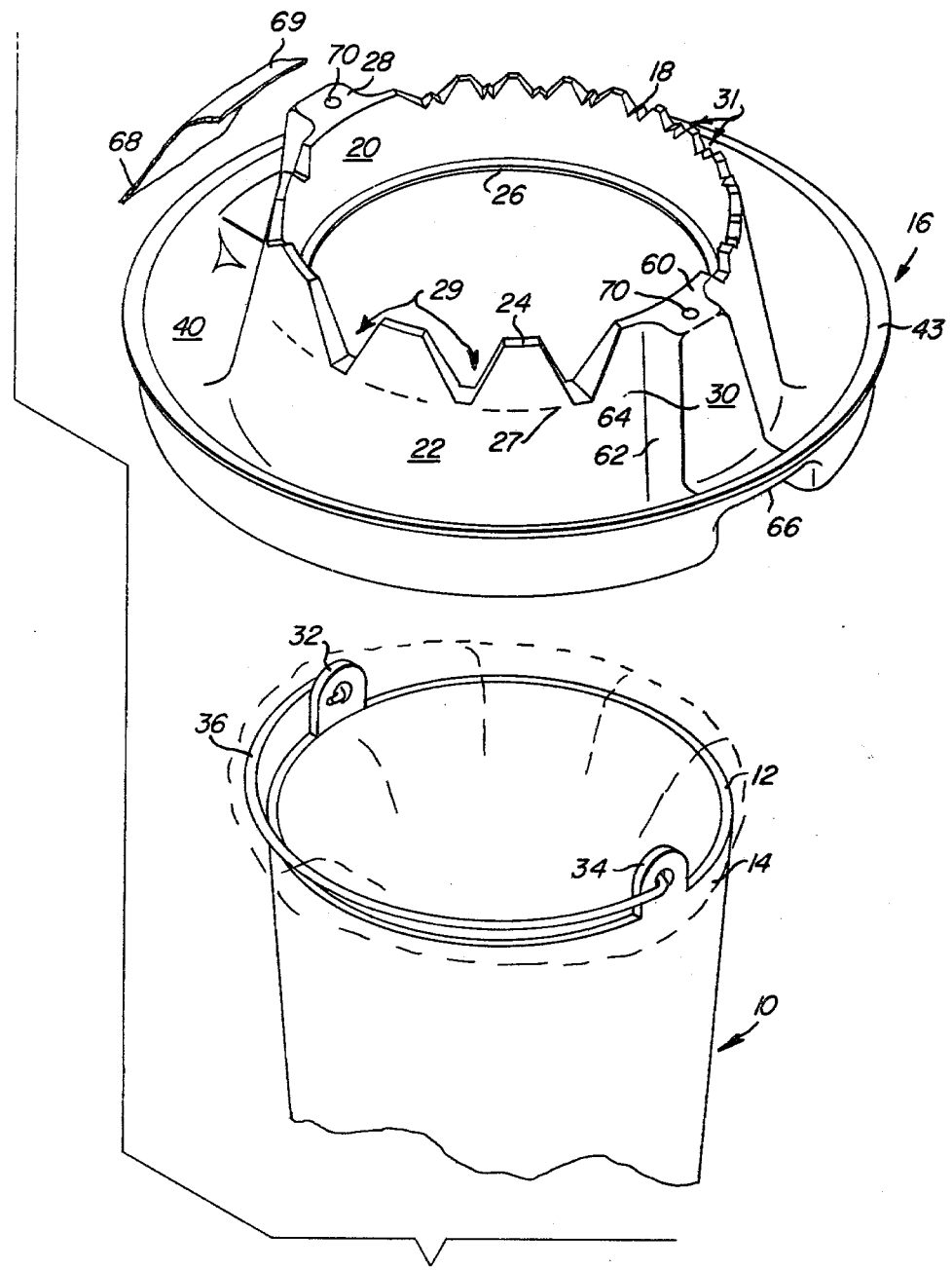
FIG. 1 is an exploded perspective view of a display and disposal apparatus of the present invention.

Referring now to FIG. 1, the present apparatus may be seen to comprise a generally cylindrical kick bucket 10 having an upper rim portion 12. A lining means comprising a disposable plastic bag 14 having an upper, open end is placed in the bucket to extend outwardly over the rim portion.

A one piece molded plastic article 16 is constructed to be supportively received over the rim 14 of the bucket 10 and the plastic bag 12. The article comprises an upwardly extending annular central portion 18 having radially spaced inner and outer sidewalls 20, 22 extending downwardly from a notched upper surface 24 to define a channel 26 in which the rim 12 of the bucket 10 is received to substantially the depth of the notched upper surface 24 as indicated by a broken line 27 connecting the bottommost surfaces of the notch portions. The article 16 is further supportively received on the bucket 10 by a pair of circumferentially opposed shoulder portions 28, 30 which receive a pair of tang portions 32, 34 extending upwardly from the rim 12 of the bucket. The tang portions 32, 34 bear therebetween an arcuate handle member 36 to form the handle portion of the bucket. The article 16 is additionally supportively received on the bucket 10 by the formation of the channel portion 26 with a greater radial width between sidewalls 20, 22 on one side of the article than on the other in order to receive the handle member 36 of the bucket.

Figure 2:
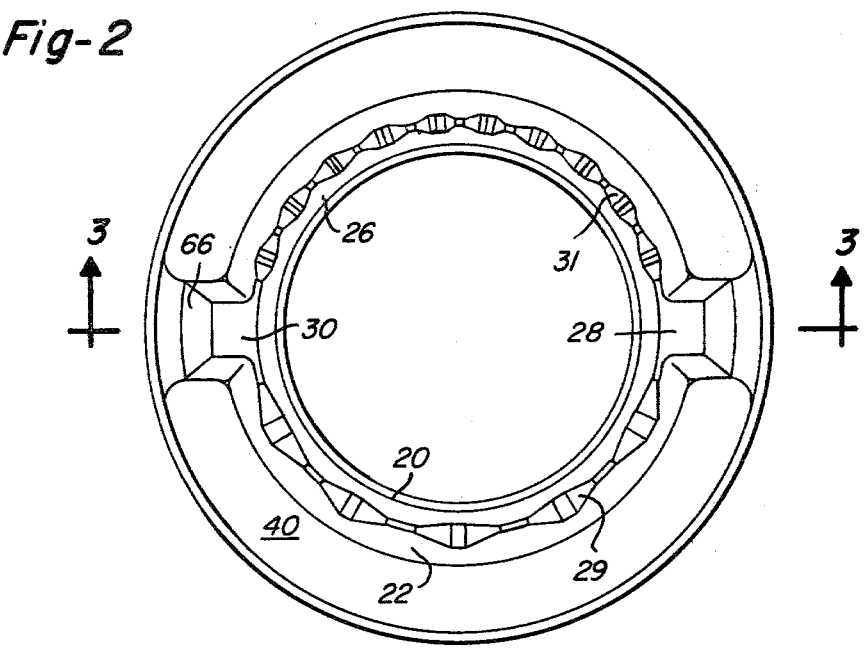
FIG. 2 is a bottom view of the one piece plastic article of the present invention.
Figure 3:
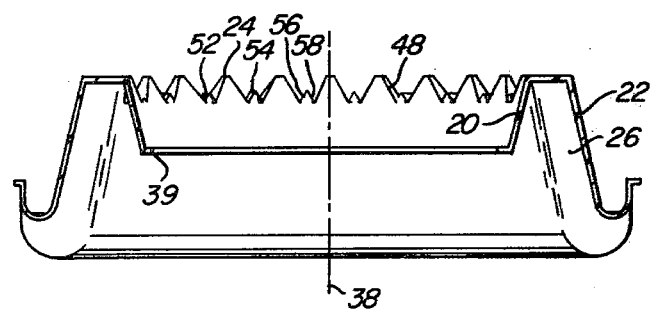
FIG. 3 is a side sectional view of the article of FIG. 2 taken along line 3—3 thereof.
Figure 4:
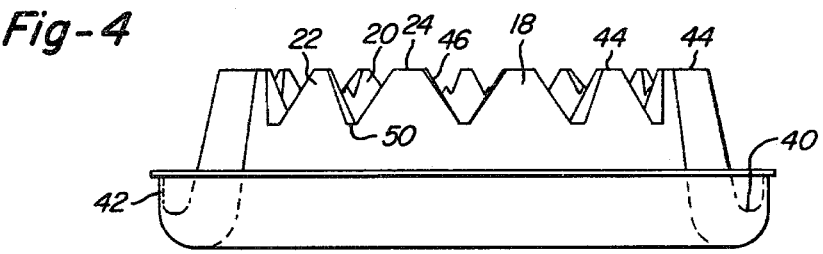
FIG. 4 is a side view of the article of FIG. 2.

Referring now to FIGS. 2-4, the article may be seen to be dividable by a line 3—3 extending diametrically between the shoulder portions 28, 30 to divide the annular central portion 18 into two generally semicircular sides, one bearing larger notched portions 29 and the other bearing smaller notched portions 31. The upper surface 24 extends in width generally perpendicularly to the central axis of the article as indicated by line 38. The inner sidewall 20 and the outer sidewall 22 extend downwardly from the upper surface 24, with the outer sidewall extending slightly radially outwardly at about a 25° angle to the inner sidewall, and downwardly about 5 inches (12.7 cm). The outer sidewall is angled outwardly slightly more on the side of line 3—3 bearing larger notched portions 29, so that the channel portion 26 will have the aforesaid greater radial width on that side. The inner sidewall 20 of the central annular portion extends substantially cylindrically with about 5⅝ in. (14.29 cm) radius of curvature and axially parallel to the axis 38 of the article, terminating approximately 2.5 in (6.4 cm) below the uppermost level of the notched upper surface 24. The inner sidewall 20 may comprise a radially inwardly extending lip portion 39 as an artifact of the molding process. The outer sidewall 22 terminates downwardly of the inner sidewall in an annular fluid receiving portion 40. The annular fluid receiving portion 40 extends uniformly circumferentially entirely about the annular central portion 18 and is formed by the circumferentially outward and upward curvature of the outer sidewall through an approximate ⅝ in. (1.6 cm) radius of curvature and an approximate 2 in. (5.1 cm) linear portion 42 extending about 7° outwardly. A handling lip portion 43 extends outwardly from the linear portion 42.

The notched upper surface 24 is arranged in a number of approximately coplanar uppermost surfaces 44, oppositely angled side surfaces 46, 48, base surfaces 50, 52, and tapered projections 54. In the regions of the notched portions 29, 31, the uppermost surfaces are about 5/16 in. (0.8 cm) wide and at the larger notched portions, about ¾ in (1.9 cm) long, and at the smaller notched portions, about ⅛ in. (0.3 cm) long. The oppositely angled side surfaces 46, 48 of the upper surface 24 extend downwardly from the uppermost surfaces, becoming gradually downwardly wider, to the base surfaces 50, 52 to define the larger and smaller notched portions 28, 31. The larger notched portions 29, there being five in the preferred embodiment, are sized for so-called lap sponges of approximate 12×12 in. (30.48×30.48 cm) or 14×14 in. (35.56×35.56 cm) gauze. The opposed side surfaces 46 of each large notch portion are thus angled relative to each other at approximately 70°, the base surface 50 therebetween being about 1 ½ in. (3.05 cm) below the uppermost surface 44 and about ¼ in. (0.64 cm) long, being upwardly curved as the sector of a circle of about ¼ in. radius. The smaller notched portions 31, there being 10 in the preferred embodiment, are sized for smaller gauze sponges, about 4×16 in. (10.16×40.64 cm), such as RAYTECH brand X-ray detectable sponges from Johnson and Johnson. The opposed side surfaces of each smaller notch portion are thus angled relative to each other at about 40°, the base surface 52 being about ¾ in (1.9 cm) below the uppermost surface. The base surface 52 of each smaller notch portion 31 preferably further comprises tapered projections 54 extending axially upwardly a short distance midway between the bottoms of the side surfaces 52 and formed of two adjacent arcuate surfaces 56, 58 about ⅜ in long and being sectors of 5/16 in. (0.8 cm) radius circles. The tapered projections provide additional frictional engagement between the sponges and the notches.

Since each shoulder portion 28, 30 is essentially identical, only one shoulder portion 30 will be described in detail. The shoulder portion 30, as shown in FIG. 1, extends circumferentially outwardly from the outer sidewall 22 such that a rectangular upper shoulder portion 60 extends outwardly of the uppermost surface 44 with side surfaces 62 each extending equally, uniformly downwardly from the shoulder portion 60 and radially outwardly from the outer side surface 22. A lateral surface 64 extends between the side surfaces 62 and the upper portion 60 and is tapered to be broader at the base portion of the shoulder portion, whereat the annular fluid receiving portion 40 is rectangularly upwardly indented to provide a handle portion 66 extending radially outwardly and axially upwardly of the fluid receiving portion.

In the preferred embodiment, the present apparatus further comprises a pair of disposable, transparent, sealable plastic bags 68 (one being shown) removably attached to an adhesive disc 70 fixed on the uppermost surface 60 of each shoulder portion. Each bag comprises a sealing flap 69 for containing the contents of the bag.

The one piece article 16 is preferably formed of high impact styrene for strength and economy and for compliance with FDA regulations. Other plastics which may be used include ABS and cellulosics. The article may be tinted green to provide better sponge contrast. The article 16 is formed from a sheet which is cut and molded to a uniform thickness of 0.050–0.065 in. (1.3–1.7 cm) in a split mold process. The article is sterilized with ethylene oxide.

Figure 5:
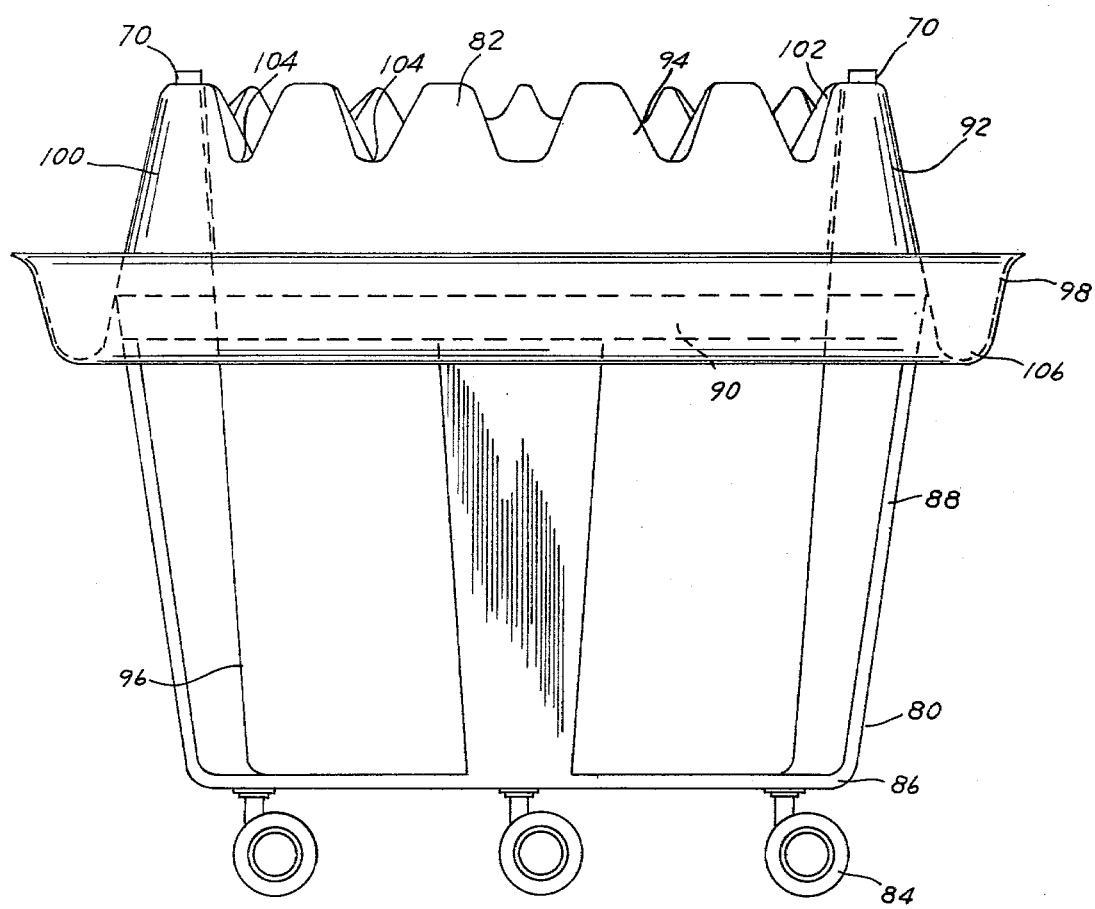
FIG. 5 is a side view of another display and disposal apparatus according to the present invention.

Referring now to FIG. 5, apparatus for enumerative display and disposal of surgical sponges is shown comprising a stand 80 which supports a unitary lining and counting member 82.

The stand 80 may be a conventional kick bucket stand having casters 84 on a bottom 86 and a number of upright supports 88 extending from the bottom at an outward angle to an upper ring 90.

The lining and counting member 82 may be used in conjunction with a standard kick bucket or in a freestanding form. It may be constructed of a rigid upper structure, as previously described, and a flexible lining, or it may be completely rigid.

The lining and counting member 82 comprises an upwardly extending annular central portion 92, defining an uppermost notched surface 94, and a lining 96 extending downwardly and inwardly of the annular central fluid portion to form a continuous container for fluids from sponges draped over the notched surface. A circumferentially outwardly extending lip 98 provides a fluid receiving portion for fluids flowing outwardly from sponges draped over the notched surface 94.

The upwardly extending annular central portion 92 defines an inner channel 100, as in the case of the embodiment of FIG. 1, which can be used to receive a kick bucket or other types of support such as the stand 80. The channel 100 presents an outwardly rounded upper surface 102 extending circumferentially around the central portion and leading to the lining 96 and the lip 98. The upper surface 102 is provided with a predetermined number of notches 104 extending circumferentially in an arcuate or V-shaped configuration. As in the case of FIG. 1, five large notches and ten small notches facilitate the sponge count.

The lining 96 forms an inner portion of the apparatus and may be of a rigid cylindrical configuration, or any other configuration, or it may be a flexible film, so long as it is continuously, sealingly joined to the annular central portion 92 so that no fluids or contaminants flowing into the lining from sponges in the notches 104 may escape the apparatus.

The lip 98 curves downwardy from the upper surface 102 and then circumferentially upwardly and outwardly to form a fluid receiving trough 106 outwardly of the upper surface. The trough 106 receives fluids and contaminants from sponges in the notches 104 to prevent fluids from running onto the stand 80 or the floor.

A pair of bag attachment means 70, as in FIG. 1, are mounted on the upper surface 102. The lining and counting member 82 is also sterilized.

In the process of the present invention, a number of kick buckets 10 are provided with disposable bags 14 or other suitable lining means and the channel portions 26 of a number of articles 16 are fitted over the rims of the buckets and the lining means therein. A supply of smaller disposable bags 68 is also provided in the operating room. As used sponges are to be counted and disposed of, one sponge is placed in each notch portion until each notch portion has one sponge. When there are 5 large sponges on the large notches or 10 small sponges on the small notches, the sponges are placed on one of the disposable bags 68 attached to the article 16. The sponges are placed in the bag by holding the bag open with one hand as the bag is then attached to the article. When the bag is loaded, it is detached from the article, folded shut through the flap portion 69, and weighed, if desired. Another bag is then attached to the article, and the notches are refilled. At the end of the procedure, the bags and the loose sponges in the sterile field are counted. If the bag count does not agree with the count of sponges used, the individual smaller bags are opened and the sponges are recounted. When the sponge counts have been verified as correct the bags and sponges are disposed of in the lining means at the close of the case.

Thus there have been provided a method and apparatus for enumerative display and disposal of surgical sponges which improves the aseptic environment and efficiency of the operating room at a relatively low cost, is disposable, and is nestable for convenient storage. The method of the present invention also permits separate handling and weighing of a number of different types of sponges.

What is claimed is:

1. A used surgical sponge display device whereby enumerative display of used surgical sponges is enhanced comprising:
    first means including an upwardly extending annular central portion having a notched upper surface with a predetermined number of spaced notches thereon for retaining used surgical sponges to facilitate their identification as to number, said annular central portion having opposed inner and outer sidewalls extending downwardly therefrom to define a channel, each said notch being defined by a pair of opposite side surfaces and a base surface extending between opposed side surfaces;
    second means including a fluid receiving portion extending circumferentially around and extending outwardly from said annular central portion for collecting and retaining the fluid from the retained used surgical sponges; and
    third means inwardly of said annular central portion and including an inner container portion having sidewalls extending downwardly from said inner sidewall of said annular central portion and a bottom for receiving and retaining said sponges and fluid from said retained sponges on said notches.

2. The device of claim 1 wherein said inner container portion is continuously sealingly attached to said inner sidewall of said annular central portion.

3. The device of claim 1 comprising five large notches and ten small notches.

4. The device of claim 1 further comprising a rollable stand detachably supporting said annular central portion.

5. The device of claim 1 wherein said inner container portion is formed of one sheet of continuous, flexible film.

6. The device of claim 1 wherein said inner and outer sidewalls are acutely angled so that said channel is narrower at the top and the side surfaces are acutely angled so that each notch is wider at the top, said base surface being shorter than said side surfaces.

7. The device of claim 1 wherein said annular central portion has opposed shoulder portions extending circumferentially outwardly from said outer sidewall for receiving the handle portion of a bucket.

8. The device of claim 1 wherein at least some of said base surfaces have tapered projections extending upwardly therefrom.

9. A used surgical sponge display device whereby enumerative display and disposal of used surgical sponges is enhanced comprising:
    an upwardly extending annular central portion having a notched upper surface with a predetermined number of spaced notches thereon for retaining used surgical sponges to facilitate their identification as to number, said annular central portion having opposed inner and outer sidewalls extending downwardly therefrom to define a channel, each said notch being defined by a pair of opposite side surfaces and a base surface extending between opposed side surfaces, said inner and outer sidewalls being acutely angled so that said channel is narrower at the top, said side surfaces being acutely angled so that each notch is wider at the top, said annular central portion having opposed shoulder portions extending outwardly of said outer sidewall for receiving the handle portion of a bucket, there being five large notches and ten small notches, said central portion having at least one adhesive element on an outer surface for removably attaching a plastic bag thereto during sponge counting;
    a fluid receiving portion extending circumferentially around and extending outwardly from said annular central portion for collecting and retaining the fluid from the retained used surgical sponges; and
    an inner container inwardly of said annular central portion, said inner container having sidewalls continuously sealingly attached to said inner sidewall and extending downwardly from said inner sidewall of said annular central portion and a bottom for receiving and retaining said sponges and fluid from said retained sponges on said notches.

* * * * *